United States Patent [19]

Frisch et al.

[11] 4,447,237

[45] May 8, 1984

[54] VALVING SLIT CONSTRUCTION AND COOPERATING ASSEMBLY FOR PENETRATING THE SAME

[75] Inventors: Eldon E. Frisch, Midland, Mich.; Leon C. Parks, Brandon, Miss.

[73] Assignees: Dow Corning Corporation, Midland, Mich.; Research Against Cancer, Inc., Jackson, Miss. ; a part interest

[21] Appl. No.: 376,002

[22] Filed: May 7, 1982

[51] Int. Cl.³ ........................ A61M 25/02; A61M 1/03
[52] U.S. Cl. .......................................... 604/175; 604/4; 604/256; 128/399
[58] Field of Search ............... 128/1 R, 399, 400–402, 128/DIG. 26; 604/4, 8, 175, 9, 256; 251/150; 141/19, 287, 329, 330, 382–386

[56] References Cited

U.S. PATENT DOCUMENTS

| | | | |
|---|---|---|---|
| 3,477,438 | 11/1969 | Allen et al. | 604/99 |
| 3,638,649 | 2/1972 | Ersek | 128/214 R |
| 3,660,345 | 5/1972 | Bobear | 260/37 SB |
| 3,671,480 | 6/1972 | Wada et al. | 260/29.1 SB |
| 3,713,441 | 1/1973 | Thomas | 128/214 R |
| 3,805,857 | 4/1974 | Johnson et al. | 141/287 |
| 3,826,257 | 7/1974 | Buselmeier | 128/214 R |
| 3,853,126 | 12/1974 | Schulte | 128/214 R |
| 3,955,594 | 5/1976 | Snow | 137/493 |
| 3,957,713 | 5/1976 | Jeram et al. | 260/32.8 SB |
| 3,998,222 | 12/1976 | Shihata | 128/214 R |
| 4,162,243 | 7/1979 | Lee et al. | 260/37 SB |
| 4,181,132 | 1/1980 | Parks | 128/399 |

*Primary Examiner*—C. Fred Rosenbaum
*Assistant Examiner*—Michelle N. Lester
*Attorney, Agent, or Firm*—Cushman, Darby & Cushman

[57] ABSTRACT

An improvement in the implantable shunt device of the type disclosed in U.S. Pat. No. 4,181,132 wherein each valving slit within the elastomeric body of the shunt is formed by a flattened sleeve of woven vascular prosthesis material presenting opposed interior surfaces interengaged when the valving slit is in a closed condition and spaced apart when the valving slit is in an open condition. The opposed surfaces of the sleeve are formed by a material having a coefficient of friction with respect to the material of the cannula insertable therethrough less than that of the elastomeric material of the body. A separate yieldable bias operable in addition to the bias provided by the elastomeric material of the body is provided for yieldably biasing the opposed surfaces of the flattened sleeve into sealed relation when in the closed interengaged condition and into sealed relation to the exterior periphery of the portion of the cannula extending therethrough when in the open spaced apart condition. The additional bias is provided by filling under pressure opposed cavities in the elastomeric body with a yieldable material so located with respect to the flattened sleeve as to transmit the pressure thereof as the additional bias of the opposed surfaces into sealed relation when in the closed interengaged condition and into sealed relation with the exterior periphery of the cannula when in the open spaced apart condition.

24 Claims, 12 Drawing Figures

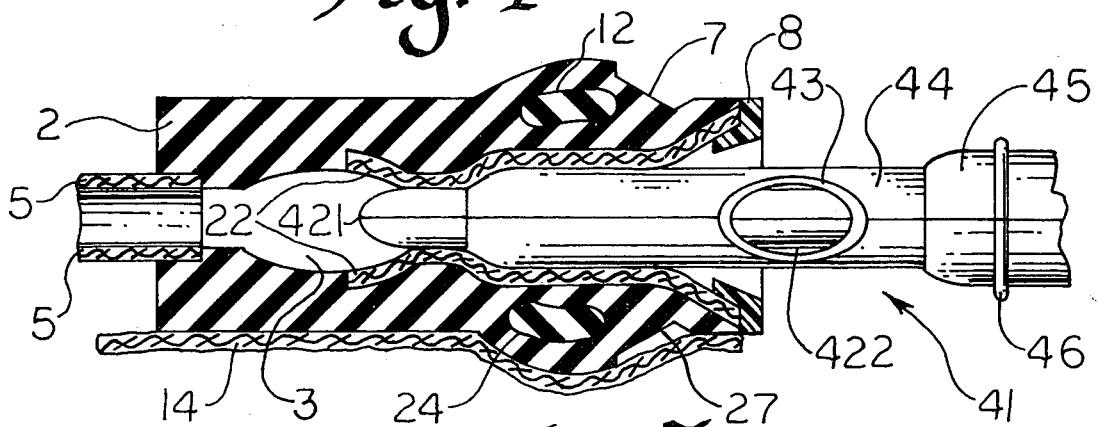
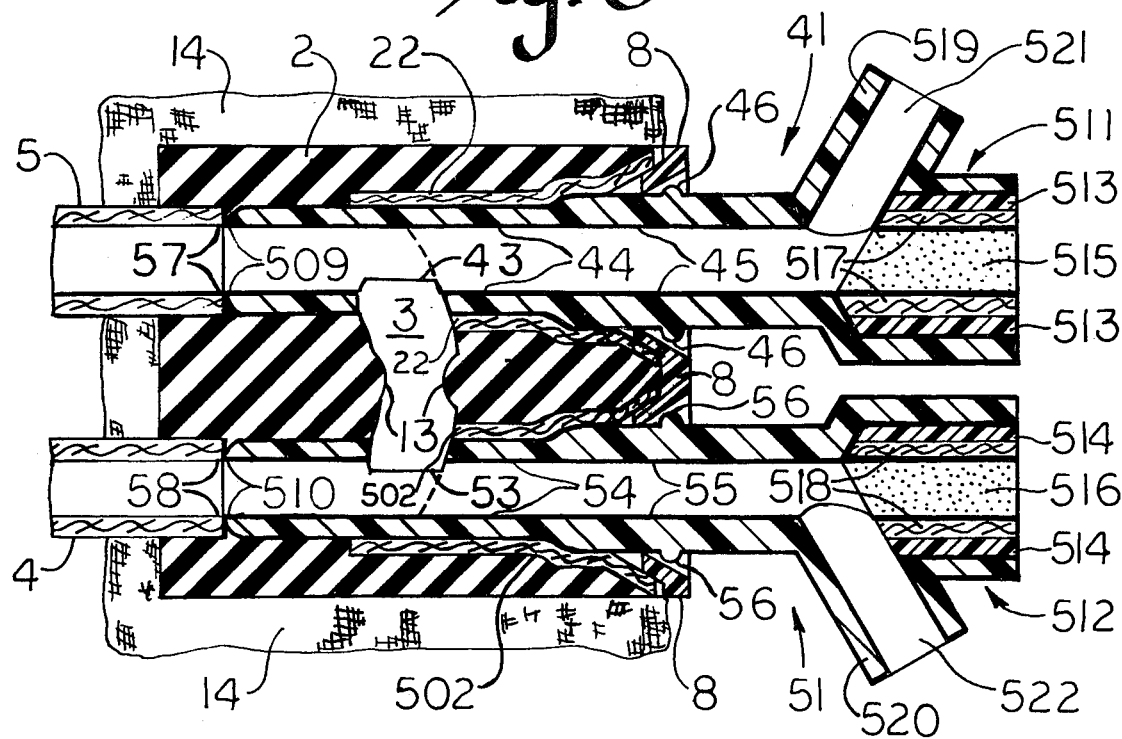
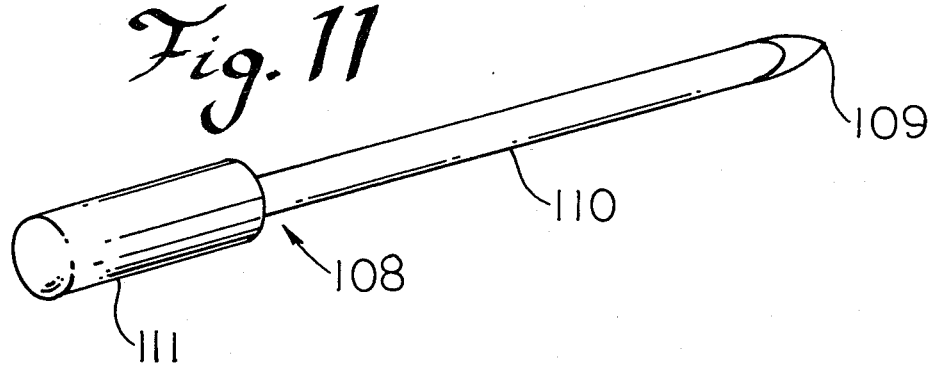

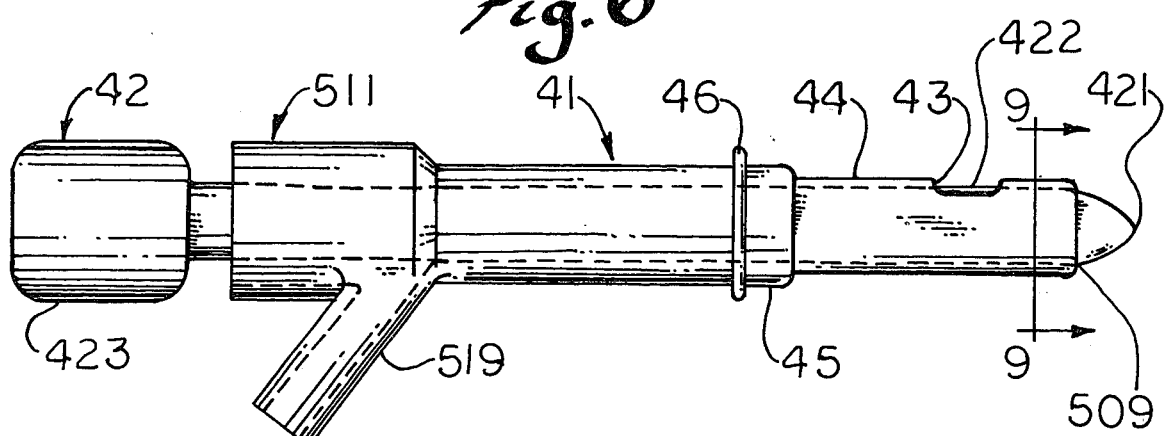
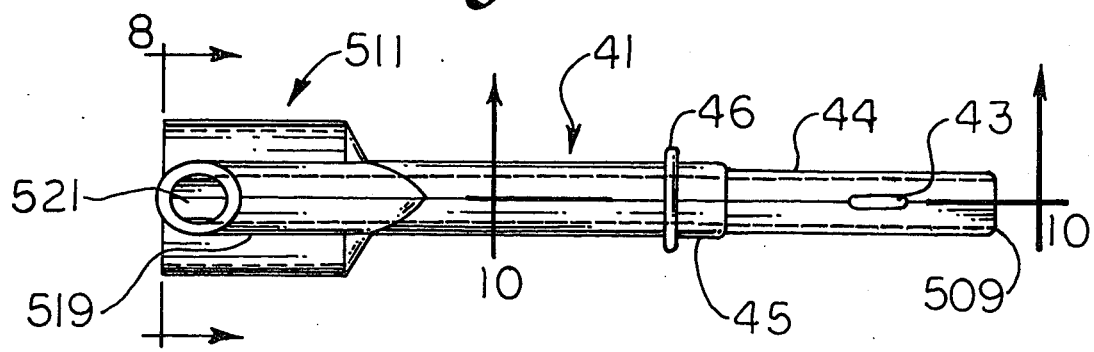
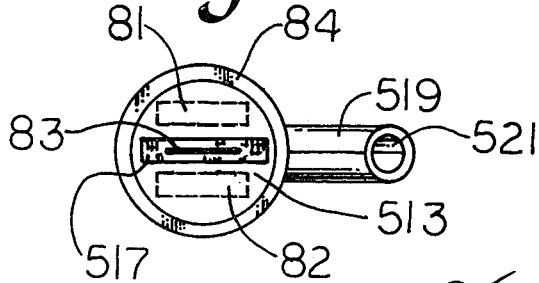
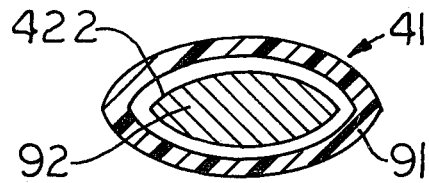
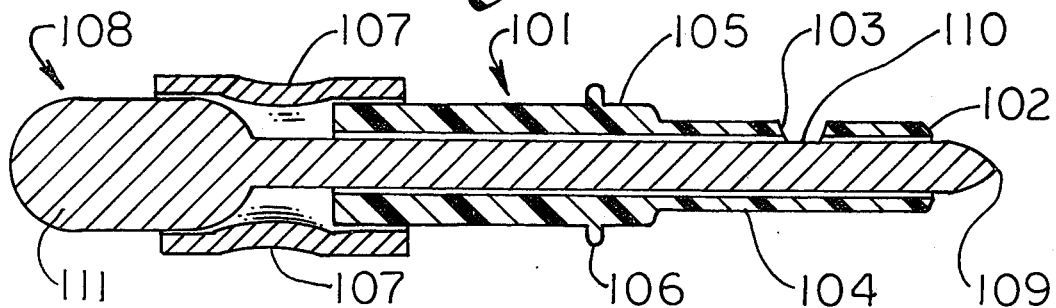

VALVING SLIT CONSTRUCTION AND COOPERATING ASSEMBLY FOR PENETRATING THE SAME

This invention relates to hyperthermic treatment for anti-cancer purposes and more specifically to improvements in the apparatus for inducing systemic hyperthermia by heating the blood of the patient in an extracorporeal circuit disclosed in U.S. Pat. No. 4,181,132, issued Jan. 1, 1980 to Leon C. Parks.

In the aforesaid Parks patent the apparatus for inducing systemic hyperthermia comprises essentially sterile tubing for defining the extracorporeal blood flow path, a pump for establishing the flow of blood through the extracorporeal flow path, a system for precisely controlling the heat of the blood moving in the extracorporeal flow path, an implantable shunt device for connection with the patient's blood system and a pair of cannula-trocar assemblies for connecting the extracorporeal circuit with the implantable shunt device. The present invention is more particularly concerned with improvements in the implantable shunt device and the cooperation between the implantable shunt device and the associated inlet and outlet cannula-trocar assemblies.

The implantable shunt device disclosed in the aforesaid Parks patent comprises essentially a body of elastomeric material defining therein an arterial passage, a spaced venous passage and a bypass conduit extending from one end of the arterial passage to one end of the venous passage. A length of woven vascular prosthesis material serves as an arterial inlet for connecting the arterial passage in communicating relation with the interior of an artery of the patient. A second length of woven vascular prosthesis material serves as a venous outlet for connecting the venous passage in communicating relation with the interior of a vein of the patient. The elastomeric body provides an outlet valving slit therein which is movable between (1) a closed condition so that blood flowing from the arterial inlet through the arterial passage will pass therefrom through the bypass conduit into the venous passage and out of the venous outlet and (2) an open condition in sealing relation with the exterior periphery of the portion of a blood withdrawing cannula extending therethrough so that blood flowing from the arterial outlet through the arterial passage will flow through the blood withdrawing cannula and the bypass conduit. A similar outlet valving slit is provided in the elastomeric body movable between (1) a closed condition so that blood flowing from the bypass conduit will pass therefrom into the venous passage and out of said venous outlet and (2) an open condition in sealing relation with the exterior periphery of the portion of a blood returning cannula extending therethrough so that the venous passage will receive blood flow both from the blood returning cannula and the bypass conduit.

In the specific disclosure contained in the aforesaid Parks patent both the outlet valving slit and the inlet valving slit are defined by opposed interior surfaces of the elastomeric material of the body, which surfaces are interengaged when the valving slit is in the closed condition and spaced apart when in the open condition. In the device described in the Parks patent the opposed interior surfaces of each valving slit are biased into the closed interengaged condition by the yieldable bias of the elastomeric material forming the body and by a U-shaped metal spring.

The functional requirements of the shunt valving slits are indeed quite severe in that they must provide a positive seal when in a closed condition, which seal must remain effective during the entire period when the shunt device is implanted in the patient. In addition to the required need for a highly effective seal when in the closed interengaged condition, the opposed surfaces of each valving slit must be capable of movement into the open spaced apart condition which is of considerable extent, so as to accommodate high flow rates requiring large cross-sectional areas in the flow path therethrough while effectively exteriorly sealing against leakage while the high flow rates are taking place over an extended period of time. Each valve slit must not only be capable of effective sealing in either the open or closed condition, but it must be capable of movement into the open condition from the closed condition in response to the insertion of the cannula-trocar assembly in such a way as to preclude tearing of the slit as a result of the penetrating forces applied, while at the same time minimizing the required penetrating forces and then to be self-biased into an effectively sealed closed condition from the open condition when the cannula of the cannula-trocar assembly is withdrawn. The present invention is directed to improved constructions which will optimize and facilitate these demanding functional requirements.

In accordance with the principles of the present invention, this objective is obtained by providing improvements in each valving slit which include the provision of a flattened sleeve within the elastomeric body presenting opposed interior surfaces interengaged when the valving slit is in the closed condition and spaced apart when the valving slit is in the open condition. The opposed surfaces of the flattened sleeve are formed by a vascular prosthesis material having a coefficient of friction with respect to the material of the cannula less than that of the elastomeric material forming the elastomeric body. In conjunction with the flattened sleeve construction, each valving slit has, in addition to the bias provided by the elastomeric material of the body, additional means within the elastomeric material of the body for yieldingly biasing the opposed surfaces of the flattened sleeve into sealed relation when in the closed interengaged condition and into sealed relation to the exterior periphery of the portion of the cannula extending therethrough when in the open spaced apart condition. The additional biasing means includes cavity means within the elastomeric body filled under pressure with a yieldable material so located with respect to the flattened sleeve as to transmit the pressure thereof as the additional bias of the opposed surfaces into sealed relation when in the closed interengaged condition and into sealed relation with the exterior periphery of the cannula when in the open spaced apart condition.

The improvements of the present invention while having specific applicability to the inlet and outlet valving slits of the shunt device disclosed in the aforesaid Parks patent, also have applicability in other situations where exterior-to-interior communicating access of a penetrating member is desirable and necessary through an exterior valving slit in communication interiorly with a blood system or circuit. For example, the improvements are applicable to the valving slit provided in the end of the cannula which enables the trocar to sealingly penetrate therein and to communicate with the blood in the circuit to which the cannula is connected. The particular construction of the flattened sleeve in conjunction with the additional yieldable pressurized biasing means is particularly effective in accomplishing the sealing functions while reducing the penetrating forces required to move the valving slit into its open condition and precluding slit damage as a result of penetration. Where the improvements are applied to fluid systems other than blood systems the material of the flattened sleeve may be varied to accommodate the fluid of the system being controlled and the material forming the exterior periphery of the insertable fluid engaging structure.

Accordingly, it is a further object of the present invention to provide apparatus of the type described for use in a pressurized fluid system capable of performing effectively the sealing and cooperative penetrating functions described above.

Another object of the present invention is the provision of a valve assembly for providing exterior access to a pressurized blood system which is constructed in accordance with the principles of the present invention in order to achieve the functions previously described.

These and other objects of the present invention will become more apparent during the course of the following detailed description and appended claims.

The invention may best be understood with reference to the accompanying drawings, wherein an illustrative embodiment is shown.

In the drawings:

FIG. 4 is an enlarged, cross-sectional view of FIG. 1 taken along section line 2—2 further showing the entry of a blood transferring cannula with its cooperating trocar assembled therein;

FIG. 5 is a cross-sectional view of the implant device of FIG. 1 along section line 5—5 further including two blood transferring cannulas fully inserted into the device;

FIG. 6 is a top plan view of a blood transferring cannula with its cooperating trocar assembled therein;

FIG. 7 is a side view of the cannula of FIG. 6;

FIG. 8 is an end view of the cannula of FIG. 7 viewed from line 8—8 showing the trocar valve and a portion of its interior detail;

FIG. 9 is a section of the cannula-trocar of FIG. 6 taken along line 9—9;

FIG. 10 is a cross-sectional view of an alternative embodiment of the cannula-trocar assembly shown in FIG. 6;

FIG. 11 is a perspective view of the trocar of FIG. 10; and

Figure 1:
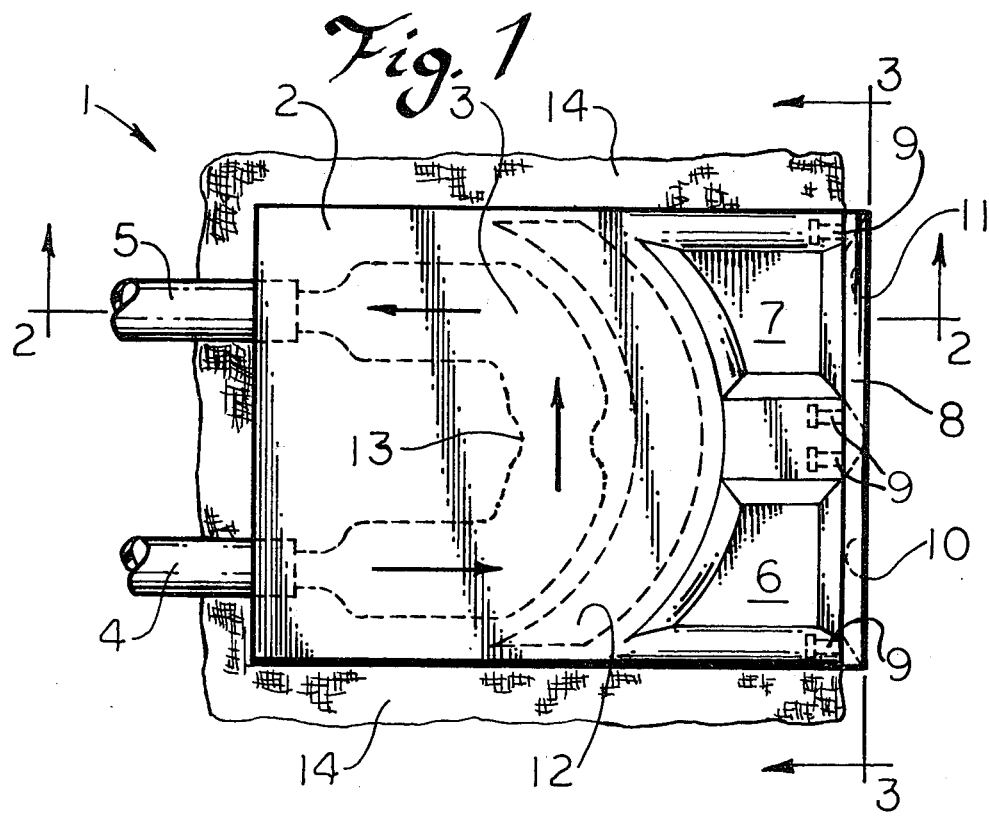
FIG. 1 is a plan view, including a portion of the internal detail thereof, of an implant device for extracorporeal circulation of blood containing the improved slit valve of the present invention.

Referring to the drawings, FIG. 1 shows one embodiment in which the improved slit valve of the present invention can be used which is to improve the self-sealing characteristics of a surgically implantable device 1 for extracorporeal circulation of blood of the type that is described in the aforesaid Parks patent. Surgically implantable device 1 is a biocompatible elastomeric body 2 containing a shunt path 3 for establishing communication with the bloodstream of a patient by means of blood inlet tube 4 and blood outlet tube 5. Communication with blood circulating through shunt path 3 is established by inserting two later-described cannula-trocar assemblies into slit valves which are located beneath indentations 6 and 7 on elastomeric body 2. The cannula-trocar assemblies are inserted through openings 10 and 11 in guideplate 8 which is affixed to elastomeric body 2 by means of four attachment pins 9 and four corresponding attachment pins located opposite pins 9 (not shown). The slit valves also extend beneath internal chamber or cavity 12 and communicate with shunt path 3. Two corresponding indentations are located directly opposite indentations 6 and 7 (see indentation 27 of FIG. 2).

Shunt path 3 contains a flow restrictor 13 which is smaller in cross-sectional area than any other portion of shunt path 3 and is used to control the maximum blood flow rate through shunt path 3. Flow restrictor 13 is curved to avoid turbulence as blood flows through shunt path 3. By adjusting the cross-sectional area of restrictor 13, the same mold with various inserts for the shunt path can be used to produce implant devices which can be used in conjunction with smaller (lower flow rate) or larger (higher flow rate) blood vessels in different parts of the body. A flow rate of a minimum of approximately 1 liter per minute through shunt path 3 is expected to be employed when an implantable device of this type is to be employed in the situation described in FIG. 12, infra.

Elastomeric body 2 can be molded from any biocompatible elastomer material that is suitable for implantation within the human body. The most commonly used and therefore preferred elastomer materials for implantation are silicone elastomers. Compositions curable to silicone elastomers are commercially available under the trademark SILASTIC ® from Dow Corning Corporation, Midland, MI. Although the exact type of biocompatible silicone elastomer to be used forms no part of the present invention, it can be preferable to use a composition which is curable to a high tear strength silicone elastomer possessing the following physical properties after an appropriate cure cycle: a durometer value of about 30–40 (Shore A, ASTM D2240), a tear propagation strength value of at least 200 p.p.i. (Die B, ASTM D624), a tensile strength value of at least 900 p.s.i. (Die C, ASTM D412), an elongation value at break of at least 500% (Die C, ASTM D412) and a modulus at 100% elongation of at least 75 p.s.i. (ASTM D412). Compositions curable to elastomers having such physical properties are known to those skilled in the art of formulating such compositions as can be seen from an examination of U.S. Pat. Nos. 3,660,345; 3,671,480; 3,957,713; and 4,162,243.

Tubes 4 and 5 are made of vascular prosthesis material. A preferred vascular prosthesis material is Cooley woven double velour DACRON ® polyester in the shape of a corrugated tube marketed commercially by Meadox Medicals, Oakland, NJ although other acceptable vascular prosthesis material can be used.

Device 1 contains a fabric layer 14 which can be fixed to the lower wall of elastomeric body 2 by some means such as a silicone adhesive or the like. Fabric layer 14 and particularly the marginal portions thereof provide for initial fixation by suture to an appropriate internal portion of the body and for subsequent semi-permanent fixation by tissue ingrowth. Fabric layer 14 can be any type of fabric, felt or other substance commonly used as a tissue ingrowth material for surgical implants such as those described in U.S. Pat. No. 3,293,663 to Cronin issued Dec. 27, 1966 and, more particularly, can be a polyester felt material commercially marketed by American GAF Corporation, New York, NY.

Figure 2:
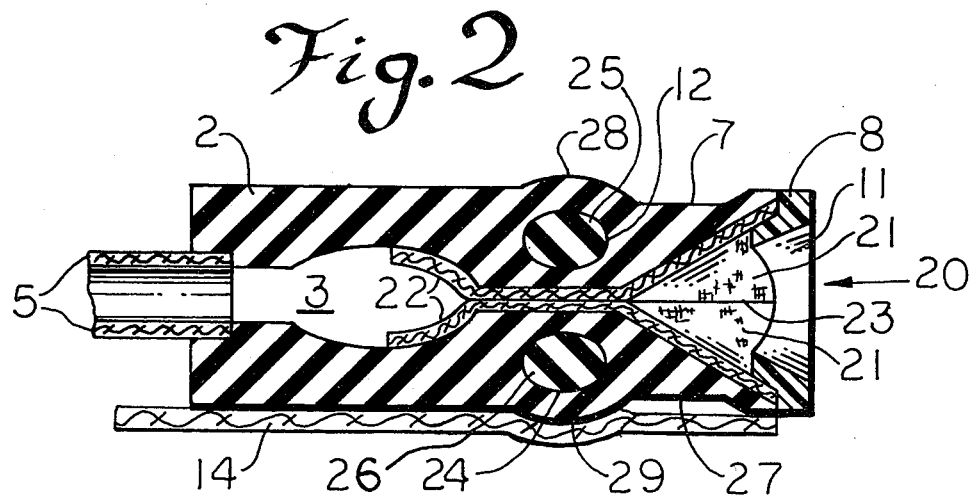
FIG. 2 is an enlarged, cross-sectional view of the device of FIG. 1 taken along section line 2—2.

The details of the improved slit valve are more clearly depicted in FIG. 2 which is a cross-sectional view of device 1 of FIG. 1 along section line 2—2 showing slit valve 20 in its closed position. Slit valve 20 is opened by inserting a cannula-trocar assembly (shown in FIGS. 4 and 5, infra) through opening 11 in guideplate 8 where it contacts the opposed interior surfaces 21 of a flattened sleeve or tube 22 defining a slit 23 of the valve. Indentations 7 and 27 in elastomeric body 2 enable the cannula-trocar assembly to initially be inserted with less force than would be needed without their presence and aid in guiding the cannula-trocar assembly into slit 23 of the valve.

It is preferable to use a flattened sleeve in the form of a tubular one-piece fabric of the type shown because the opposed interior surfaces 21 thereof have a lower coefficient of friction with respect to the material of the cannula to aid in reducing the amount of force needed to insert a cannula-trocar assembly. A preferred woven vascular prosthesis material for this purpose is a straight, uncrimped, compacted and heat set tube of Microvel double velour DACRON ® polyester fabric commercially marketed by Meadox Medicals. It will be understood that other forms of sleeves of vascular prosthesis material may be utilized such as a tubular porous structure of polytetrafluoroethylene commercially marketed under the name GORE-TEX ® from W. L. Gore and Assoc., Newark, Delaware, 19711. As is commonly known, a DACRON ® polyester fabric of woven vascular prosthesis material tends to become lightly coated with clotted blood and thereafter a neointima forms. This coating can serve to improve the sealing characteristics of such fabric materials. Therefore, fabric linings of this type are utilized when the improved slit valves of the present invention are used in applications involving contact with blood. The inner circumference of the tube is selected to match the largest circumference of the cannula to be inserted.

The above Microvel double velour DACRON ® polyester tube can be prepared for use as a slit valve by pressing out an appropriate length of the tube to a completely flat, wrinkle-free shape to form slit 23 and then applying, such as by calendering a layer of uncured silicone elastomer material on the top and on the bottom of the flattened tube with an amount of pressure that is sufficient enough to allow the elastomer composition to penetrate into the outer layer of the tube, but not sufficient enough to allow the elastomer composition to penetrate into the interior of the slit 23. The elastomer is then cured to produce a reasonably strong fabric sleeve 22 which will not easily be cut by the tip or exposed sharp edges of the trocar, but will possess a low friction surface which allows relatively easy insertion of the cannula-trocar assembly. 12.

Figure 3:
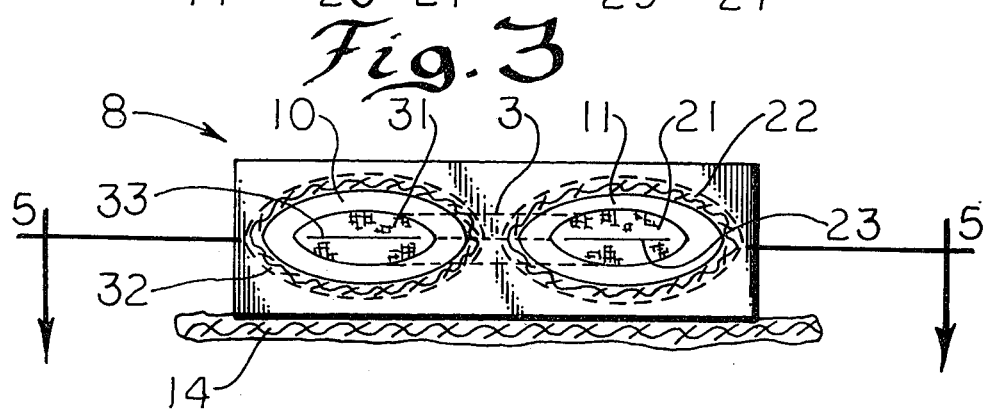
FIG. 3 is an end view of the implant device of FIG. 1 viewed from line 3—3.

One of the above-described elastomer coated flattened fabric sleeves is adhered to the outside of opening 11 on guideplate 8 as shown in FIG. 2 and the same procedure is followed for opening 10 as can be seen in FIG. 3, which is an end view of the device 1 of FIG. 1. FIG. 3 shows that flattened fabric sleeves 22 and 32 are affixed to the outside of openings 10 and 11 on guideplate 8 which are located within elastomeric body 2. The interior surfaces 21 and 31 of flattened fabric sleeves 22 and 32 which contain slits 23 and 33 are readily visible. Guideplate 8 can be manufactured from a rigid biocompatible material such as metal (e.g. stainless steel) or a hard plastic material such as polysulfone or polymethylmethacrylate to guide the cannula-trocar assembly to slits 23 and 33 respectively. Preferably, guideplate 8 is injection molded from UDEL ® Medical Grade Polysulfone commercially marketed by Union Carbide Corp., New York, NY. When polysulfone is used with the DACRON ® polyester tubes described above, the end of each flattened fabric sleeve 22 and 32 is dipped in methylene chloride (a solvent for polysulfone) and pressed into openings 10 and 11 to adhere the flattened fabric sleeves to the guideplate 8. The guideplate 8 with the attached flattened fabric sleeves is then heated in a vacuum oven at 40° C. for a sufficient amount of time (about one hour) to remove any residual methylene chloride.

The guideplate with the attached flattened fabric sleeves is then placed in an appropriately shaped transfer mold and elastomeric body 2 is formed using conventional molding techniques and cure cycles. Other molding techniques can also be used.

Referring back to FIG. 2, in addition to being compressed together by the elastomeric body 2 located around fabric sleeve 22, the present invention provides a yieldable biasing means in addition to the elastomeric body itself to improve the sealing characteristics of slit 23. As shown, the additional biasing means is in the form of a chamber or cavity 12 formed during the molding process within elastomeric body 2. Chamber 12 is situated in pressure applying relation to the flattened sleeve 22. Specifically it is on one side of and extends horizontally over the widest portion of the slit valve 20, i.e., extends horizontally over slit 23, perpendicular to the longest portion of slit valve 20. In this preferred embodiment, chamber 12 extends from one side of the device 1 over both slit valves to the other side. Chamber 12 should be located as close to flattened fabric sleeve 22 as possible to maximize and most evenly distribute the amount of pressure exerted against the flattened fabric sleeve 22 when chamber 12 is filled with a pressurizing yieldable material 25 of a nonmetallic, flexible composition. In the preferred embodiment depicted, pressurizing material 25 is shown as a cured silicone elastomer formed by injecting a composition curable to a silicone elastomer into chamber 12 under pressure and thereafter curing it in its pressurized state. The pressurizing yieldable material can be any nonmetallic and flexible composition or compound, whether fluid or solid, which is capable of being retained under pressure within the chamber for the useful life of the device. Examples of such materials are cured silicone elastomers, particularly those which are reasonably resistant to the effects of compression set, a polydiorganosiloxane fluid which is substantially impermeable to the elastomer body in which the chamber is formed (e.g., a fluorinated polyalkylsiloxane fluid such as poly(3,3,3-trifluoropropylmethylsiloxane) is substantially impermeable to a silicone elastomer which is substantially composed of a cross-linked polydimethylsiloxane), and vegetable oils such as cottonseed oil. The aforementioned materials are particularly useful when the elastomeric body in which the chamber is placed is a cured silicone elastomer. Preferably, the chamber is filled with a composition that is curable to form a silicone elastomer such as DOW CORNING ® MDX-4-4210 Clean Grade Elastomer which forms a polydimethylsiloxane elastomer upon curing.

Figure 12:
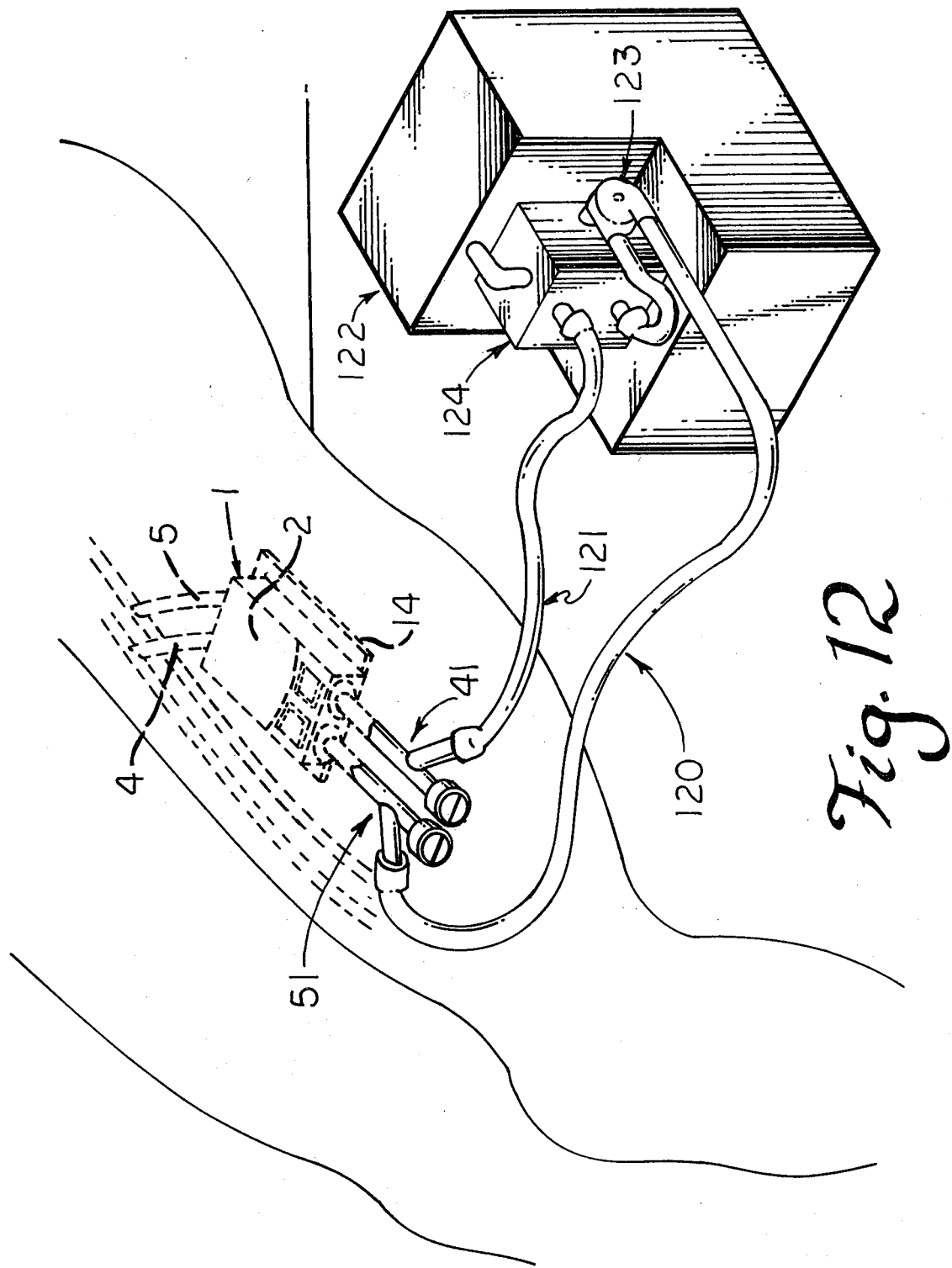
FIG. 12 is a perspective view illustrating one method of using an implant device embodying the principles of the present invention.

Some silicone elastomers have a greater tendency than others to acquire a compression set as a result of the pressure exerted on the elastomer filled chamber when a cannula is present in the slit valve and the type of silicone elastomer selected should be tested in the device before it is used. The aforementioned DOW CORNING ® MDX-4-4210 was found to be reasonably resistant to the effects of compression set. The elastomer used to manufacture elastomeric body 2 should also be reasonably resistant to compression set. Overpressurizing the chambers to resist a much higher than anticipated pressure from shunt path 3 can also reduce the effects of compression set. When the aforementioned silicone elastomer was injected in the manner later described, it was found to be useful in reliably sealing against at least 300 mm Hg (millimeters of Mercury) test pressure from shunt path 3 which is more than the maximum pressure generally expected to be found (about two and one-half times the normal physiological blood pressure level) when the implant device 1 is surgically implanted as shown in FIG. 12 in communication with the femoral artery and vein of a patient. Although fluids do not acquire a compression set, cured silicone elastomers are preferred over fluids because there is very little possibility that the contents of the chamber will escape in the event that the chamber should be pierced by a trocar or other object.

The purpose for pressurizing chamber 12 is to urge one interior surface 21 of flattened fabric sleeve 22 next to chamber 12 against the opposite interior surface thereof to render slit 23 when in a closed condition self-sealing against the pressure exerted by the bloodstream flowing through shunt path 3 in an effective, simple and reliable manner which does not require the use of an internal or external metallic spring (see FIG. 4 of the aforementioned Parks patent) or clamp to render slit valve 20 self-sealing. For applications wherein the pressure exerted by the blood flowing through shunt path 3 is low, it may be possible to simply rely upon the resistance against the pressurizing yieldable biasing means that is exerted by the portion of elastomeric body 2 that is situated on the other side of the flattened fabric sleeve 22 and is opposite to and extends horizontally over the area of the slit valve covered by the pressurizing yieldable biasing means to provide an improved seal. This portion of elastomeric body 2 would then act as a pressure-resisting means which cooperates with the pressurizing yieldable biasing means.

However, it is preferable to provide the improved slit valve of the present invention with a cooperating pressure-resisting means situated on the other side of each slit valve which means is opposite to and extends horizontally over the area of each slit valve covered by the pressurizing means. This pressure-resisting means can take the form of a rigid bar or rod of a biocompatible metal such as stainless steel or of a resin such as polysulfone or polymethylmethacrylate or preferably, as shown, is in the form of a pressurized chamber of the same type and shape as is used to provide the pressurizing yieldable biasing means already described. Other pressure-resisting means will be apparent to those skilled in the art. In some applications, it may be preferable that the pressurizing means and the pressure-resisting means be spread over as large an area of the slit valve as possible to insure even pressure against the slit and optimum sealing of the same.

As previously indicated in the preferred embodiment depicted in FIG. 2, the pressure-resisting means is a chamber 24 of the same size and configuration as chamber 12 filled with a pressurizing yieldable material 26 of a nonmetallic and flexible composition which in this embodiment is a cured silicone elastomer formed in the same manner as described above for chamber 12. The pressurizing yieldable material 26 can also be one selected from the same materials described as being useful for pressurizing material 25. As a result of the pressure in chamber 12 and 24, the elastomeric body 2 may generally exhibit bulges at 28 and 29 as it resists the pressure exerted against it by the pressurizing material 25 and 26.

Referring to FIG. 2, flattened fabric sleeve 22 extends from guideplate 8, between the pressurizing means and the yieldable biasing means and partially extends into and forms part of the interior surface of shunt path 3. Shunt path 3 has a smooth interior to provide a smooth and non-turbulent flow of blood through shunt path 3 and out tube 5 to reduce the possibility that blood clots will form in shunt path 3 during use.

Once the pressure expected from the bloodstream flowing through shunt path 3 is determined, chambers 12 and 24 can be pressurized to seal against a preselected level of pressure as follows. Two pieces of tapered polyethylene sheeting (16 inches long, 0.001 inches thick, 5/16 inches wide at one end and 11/16 inches wide at the opposite end) are heat-sealed together along two non-parallel lines to create a channel in the middle of the sheets. When a test fluid is passed through the channel between the two sheets of heat-sealed polyethylene and meets a pressure of equal magnitude, but perpendicular to its direction of flow, the flow of test fluid through the channel ceases 100%. After the channel-containing sheet is determined to be leak free and the flow through the channel is determined to stop at 200 mm Hg test fluid pressure when channel-containing sheet is placed between two platens held together by an ordinary blood pressure measuring cuff which has been pressurized to 200 mm Hg, it is then inserted through slit 23 (in this case, the slit being tested was ⅜ inches wide) by means of two metal shims which are then removed, thereby leaving the channel-containing polyethylene sheet in the slit valve.

To prepare a device containing a valve capable of sealing against at least 300 mm Hg pressure, one end of the channel-containing polyethylene sheet was connected to a source of a pressurized test fluid (water) containing a pressure gauge. A pressurizable syringe having a 19 gauge needle affixed thereto was filled with de-aired DOW CORNING ® MDX-4-4210 Clean Grade Elastomer. That curable elastomer composition was injected into one of the empty sealed chambers while the air was vented from the other side using a 20 gauge needle until the chamber was filled, but not pressurized. The opposite chamber was then filled while the air was vented and then filling under pressure (without venting) was continued until the test fluid did not begin to flow through the channel-containing polyethylene sheet until a test fluid pressure of 375 mm Hg was reached. The second chamber was then reentered and filled with the curable elastomer composition (without venting) until test fluid did not begin to flow through the channel-containing polyethylene sheet until a test fluid pressure of 750 mm Hg was reached. The channel-containing polyethylene sheet was removed and the device was placed in an oven at 350° F. for 15 minutes to cure the elastomer composition. After the device cooled to room temperature, the channel-containing polyethylene sheet was reinserted and the pressure was raised to a point where the test fluid just began to flow through the channel. That amount of pressure is the pressure which the valve is capable of resisting and was generally found to be about 600–650 mm Hg for devices made in this manner. Other methods for checking pressure at which the valve begins to open will be evident to those skilled in the art. It is best to over-pressurize the chambers to insure that the slit valve will seal against the pressure exerted by the bloodstream and to provide a safety margin in the event that the cured elastomer 25 should take on more than the anticipated amount of compression set. It will, of course, be readily apparent that given the above descriptions, the improved slit valve of the present invention can be made to seal against a variety of preselected pressures in very simple and reliable manner, which is another advantage of the present invention.

FIG. 4 is an enlarged cross-sectional view of the device of FIG. 1 taken along section line 2—2 further showing the entry of a blood transferring cannula 41 with its cooperating trocar shown as the blade portion 422 inserted therein. Cannula 41 contains an opening 43 which allows blood to enter the interior of cannula 41 when the blood contacting portion 44 of cannula 43 is fully inserted into the slit valve in addition to that passing through shunt path 3. As is best shown in FIG. 5, the sealing portion 45 of cannula 41 has a larger circumference (a 10% larger circumference works quite well) than the blood contacting portion 44 so that it engages in a sealing relationship with the interior of flattened fabric sleeve 22 (which has an interior circumference slightly less than that of sealing portion 45) when the cannula is inserted into the slit valve as far as stop 46 will permit. Trocar tip 421 passes through the opening in guideplate 8 and spreads flattened fabric sleeve 22 apart as it guides the tapered end of blood contacting portion 44 of cannula 41 along with it through flattened fabric sleeve 22 to establish communication with shunt path 3. Pressurized chamber 12 and 24 and indentations 7 and 27 are pushed out of the way as the cannula is inserted.

FIG. 5 is a cross-sectional view of the device of FIG. 1 along section line 5—5 shown in FIG. 3 which further includes two blood transferring cannulas fully inserted into the device. Cannulas 41 and 51 are fully inserted through flattened fabric sleeves 22 and 502 (which form the slit valves) until blood openings 43 and 53 are placed in the shunt path 3. The positioning of openings 43 and 53 is determined by the position of stops 46 and 56 on cannulas 41 and 51 since the cannulas are inserted through openings in guideplate 8 until each stop contacts the hard surface of guideplate 8. After the cooperating trocars (not shown) are removed from valves 511 and 512, openings 509 and 510 allow blood flowing through tube 4 to enter blood withdrawing cannula 51 where it can be withdrawn through opening 522 in blood removal side tube 520 while some of the blood can flow through opening 53 through shunt path 3 past restrictor 13 and on through opening 43 into blood returning cannula 41 where it can be mixed with blood being sent through opening 521 in blood returning side tube 519 and returned to the patient's bloodstream through tube 5. The manner in which flattened fabric sleeves 22 and 502 receive cannulas 41 and 51 can be seen by referring to the positioning of blood contacting portions 44 and 54 and sealing portions 45 and 55 of the cannulas. Sealing portions 45 and 55 are of almost the same circumference as the openings in guideplate 8 so that each cannula is securely affixed to the device after insertion up to stops 46 and 56.

The blood transferring cannulas shown in FIGS. 5-8 have slit valves 511 and 512 attached to the end of each cannula to allow a trocar to be inserted and removed from the cannula with a minimum loss of blood. This exhibits another opportunity to use the improved slit valve of the present invention which is to improve the sealing characteristics of the valve found on the cannula described in the aforementioned Parks patent. Valves 511 and 512 are shown as being surrounded by an elastomeric body 513 and 514 which can be of any elastomeric material which is suitable for contact with body fluids such as blood, and preferably is of the same type of elastomer from which elastomeric body 2 is manufactured. A trocar is passed over inner surfaces 515 and 516 of a one-piece tubular flattened fabric sleeve bounded on both sides by the edges 517 and 518 of a flattened fabric sleeve of the same type as was described above with reference to flattened fabric sleeve 22 of FIG. 2.

Referring to FIG. 6 which is a top plan view of blood transferring cannula 41 having a cooperating trocar 42 inserted therein, and FIG. 7 which is a side view of cannula 41 without a trocar, the details of the blood opening 43, blood contacting portion 44, sealing portion 45, stop 46, valve 511 and blood returning tube 519 can be readily seen. Trocar 42 is composed of a tip 421 which is adapted to pass through opening 509 in cannula 41, a blade portion 422 partially shown through opening 43 and handle portion 423. The same type of cannula can be fully seen from a perspective view in FIG. 11. While it is not shown, it can be preferable to add a sealing portion and a stop to the trocars 42 and 108 of the same type as is shown as 45 and 46 for cannula 41 to insure that the trocar forms a tight seal when the trocar is fully inserted within valve 511. A guideplate could also be fitted to the end of valve 511 if desired. FIG. 7 also shows opening 521 in blood returning side tube 519.

Cannula 41 can be manufactured from any rigid material which is suitable for contact with the human body and has a sufficient amount of strength to be used for this purpose. Examples of such materials are metals such as stainless steel and hard plastic materials such as polysulfone and polymethylmethacrylate. Polysulfone is a preferred material since it is less expensive to fabricate than metal, can be sterilized and due to its lower cost can be discarded after a single use. Likewise, the trocar can be made of the same materials as the cannula.

FIG. 8 is a rear view of cannula 41 having trocar slit valve 511 containing an elastomeric body 513 surrounding flattened fabric sleeve 517 surrounded by an internal pressurizing yieldable biasing means which is a pressurized chamber 81 and an internal pressure-resisting means which is also a pressurized chamber 82, both of which chambers are formed within elastomeric body 513 and are filled with a pressurizing yieldable material of the same type that was described above with reference to the implant device of FIG. 2 and serve to improve the sealing characteristics of slit 83. Slit valve 511 is shown as being a part of and surrounded by the same rigid material 84 from which cannula 41 is manufactured, but the valve can be a separate piece in the form of an appropriately shaped elastomeric body containing the aforementioned pressurizing and pressure-resisting means situated about a slit which may or not be surrounded by the flattened fabric sleeve described above. For example, a slit valve of the type shown as 511 could be a single elastomeric body where surrounding portion 84 is also an elastomeric material such as the elastomeric tube 107 shown in FIG. 10 which surrounds the valve portion and extends out further so as to be capable of being slipped over the end of a cannula or other tube in the manner elastomeric tube 107 is slipped over cannula 101 in FIG. 10.

FIG. 9 is a section of the cannula-trocar assembly of FIG. 6 along line 9—9 showing the biconvex lens shape of cannula 41 composed of polysulfone plastic 91 and cooperating biconvex lens cross-sectionally shaped trocar blade 422 composed of stainless steel 92, but the trocar is preferably made of polysulfone.

FIG. 10 is a cross-sectional view of an alternative embodiment of cannula-trocar shown in FIG. 6 which is composed of that portion of cannula 41 which begins at section line 10—10 and extends in the direction of the arrows up to opening 509. Thus cannula 101 has opening 102 through which tip 109 of trocar 108 is passed. Cannula 101 further includes opening 103, blood contacting portion 104, sealing portion 105 and stop 106. A tight fitting elastomeric tube which can be of silicone elastomer is fitted over the end of cannula 101 opposite opening 102 and over the handle 111 of trocar 108 to form a tight seal. After the cannula-trocar assembly is inserted into a surgically implanted device of the type described above, trocar 108 is withdrawn and a hemostat is placed over the middle of elastomeric tube 107 to restrict the flow of blood out of the tube while the trocar 108 is removed and an appropriately sized connector is fitted into tube 107 for attachment to a unit as shown in FIG. 12. This embodiment eliminates the need for a valve and reduces the cost of the cannula. Cannula 101, as well as blood withdrawal and return tubes 519 and 520, can be fitted with annular raised ridges (not shown) at the ends of the cannula and/or tubes to further insure that any tubes attached to the cannula or tubes do not leak.

FIG. 11 is a perspective view of cannula 108 of FIG. 10 showing tip 109, blade 110 and handle 111.

FIG. 12 is a perspective view illustrating one method of using the improved implant device of the present invention for effecting hyperthermic treatment of cancer patients in the manner described in the aforementioned Parks patent. Referring to FIG. 12, implant device 1 of FIG. 1 is surgically implanted in the left leg of a patient by suturing the device 1 by means of fabric layer 14 to the rectus femoris muscle of the leg. Tube 4 is sutured to the femoral artery and tube 5 is sutured to the femoral vein to establish communication with the patient's bloodstream. Cannulas 41 and 51 have been passed through the skin of the patient and are inserted within implant device 1. Tube 120 is attached to blood withdrawing cannula 51 and blood is drawn through a sterile tube 120 from the femoral artery through pump 123 through a heat exchanger assembly 124 which raises and maintains the blood passing through it at a specified temperature (generally between 41.5° C. to 43° C.) by means of a control device, generally indicated at 122. The heated blood is returned through sterile tubing 121 leading to blood returning cannula 41 which then returns the heated blood to the femoral vein through tube 5. Further details on the hyperthermia process for treating cancer patients, including other details on the construction of the implant device, the use and implantation details, advantages of the device and the like can be found in the aforementioned Parks patent, which is hereby incorporated by reference, since the present invention relates to a device of the type described therein which possesses improved sealing characteristics as a result of the application of the principles of the present invention.

As noted earlier, the improved valving slit of the present invention can also find application in other areas and need not be limited to implant devices for hyperthermic treatment. A similar type of implant device (suitably miniaturized) could also be used to provide access to the blood for hemodialysis treatment. The improved slit valve itself can be used as described above at the end of a blood contacting cannula. When devices employing the improved slit valve of the present invention are to be used in contact with blood, it can be preferable to coat all of the blood contacting surfaces of the cannulas 41 and 51, tubing 120 and 121, elastomeric bodies 2, 513, and 514, shunt path 3 and any other blood contacting areas where thrombosis could become a problem with one of a number of known anticoagulant coatings. A suitable coating material for this purpose is manufactured under the trademark TDMAC ®/Heparin which is a Tridodecylmethylammonium chloride/-Heparin complex that is available from Battelle Laboratories, Columbus, OH.

The term woven as used herein to describe the sleeve fabric is not limited to a sleeve produced on a weaving loom but comprehends sleeves produced on knitting, braiding or other similar machines.

Other modifications and variations of the improved slit valve of the present invention and of devices embodying the same will become apparent to those skilled in the art from an examination of the above specification and drawings. Therefore, other variations of the present invention may be made which fall within the scope of the appended claims even though such variations were not specifically discussed above.

What is claimed is:

1. In an implant for use with an apparatus providing an extracorporeal blood flow path extending from a blood withdrawing cannula cooperable with said implant to a blood returning cannula cooperable with said implant, said implant comprising a body of elastomeric material having means therein defining an arterial passage, a spaced venous passage, and a bypass conduit extending from one end of said arterial passage to one end of said venous passage, arterial inlet means for connecting said arterial passage in communicating relation with the interior of an artery, venous outlet means for connecting said venous passage in communicating relation with the interior of a vein, outlet valving slit means in said elastomeric body movable between (1) a closed condition so that blood flowing from said arterial inlet means through said arterial passage will pass therefrom through said bypass conduit into said venous passage and out of said venous outlet means and (2) an open condition in sealing relation with the exterior periphery of the portion of a blood withdrawing cannula extending therethrough so that blood flowing from said arterial outlet means through said arterial passage will flow through said blood withdrawing cannula and said bypass conduit and inlet valving slit means in said elastomeric body movable between (1) a closed condition so that blood flowing from said bypass conduit will pass therefrom into said venous passage and out of said venous outlet means, and (2) an open condition in sealing relation with the exterior periphery of the portion of a blood returning cannula extending therethrough so that said venous passage will receive blood flowing both from said blood returning cannula and said bypass conduit, the improvement which comprises each valving slit means comprising:

flattened sleeve means of vascular prosthesis material within said elastomeric body presenting opposed interior surfaces interengaged when said valving slit means is in said closed condition and spaced apart when said valving slit means is in said open condition, and means operable in addition to the bias provided by the elastomeric material of said body for yieldably biasing the opposed surfaces of said flattened sleeve means into sealed relation when in said closed interengaged condition and into sealed relation to the exterior periphery of the portion of the cannula extending therethrough when in said open spaced apart condition, said additional biasing means including cavity means having a yieldable material under pressure therein so located with respect to said flattened sleeve means as to transmit the pressure thereof as the additional bias of the opposed surfaces into sealed relation when in said closed interengaged condition and into sealed relation with the exterior periphery of the cannula when in said open spaced apart condition.

2. The improvement as claimed in claim 1 wherein said elastomeric body is manufactured from a cured silicone elastomer and the yieldable material within said cavity means is selected from the group consisting of a cured silicone elastomer, a polydiorganosiloxane fluid which is substantially impermeable to the silicone elastomer body and vegetable oils.

3. The improvement as claimed in claim 2 wherein said cavity means includes opposed cavities.

4. The improvement as claimed in claim 1, 2 or 3 wherein said yieldable material is a cured silicone elastomer.

5. The improvement as claimed in claim 1, 2 or 3 wherein said yieldable material is initially in a form capable of being injected into said cavity means under a sufficient amount of pressure to seal against a pressure of at least 300 mm Hg from the blood.

6. The improvement as claimed in claim 1, 2 or 3 wherein the material of said flattened sleeve means is woven polyester.

7. A valve assembly for providing exterior access to a pressurized blood system comprising
a body of elastomeric material,
flattened sleeve means of vascular prosthesis material within said elastomeric body biased into a closed condition for sealingly containing the pressurized blood in communication therewith and movable into a seal maintaining open condition in response to the insertion of an exterior access member therethrough, said flattened sleeve means having opposed interior surfaces interengaged when said valving slit means is in said closed condition and spaced apart when said valving slit means is in said open condition, and means operable in addition to the bias provided by the elastomeric material of said body for yieldably biasing the opposed surfaces of said flattened sleeve means into sealed relation when in said closed interengaged condition and into sealed relation to the exterior periphery of the portion of the access member extending therethrough when in said open spaced apart condition, said additional biasing means including cavity means within said elastomeric body having a yieldable material under pressure therein so located with respect to said flattened sleeve means as to transmit the pressure thereof as the additional bias of the opposed surfaces into sealed relation when in said closed interengaged condition and into sealed relation with the exterior periphery of the access member when in said open spaced apart condition.

8. A valve assembly as claimed in claim 7 wherein said elastomeric body is manufactured from a cured silicone elastomer and the yieldable material within said cavity means is selected from the group consisting of a cured silicone elastomer, a polydiorganosiloxane fluid which is substantially impermeable to the silicone elastomer body and vegetable oils.

9. A valve assembly as claimed in claim 8 wherein said cavity means includes opposed cavities.

10. A valve assembly as claimed in claim 7, 8 or 9 wherein said yieldable material is a cured silicone elastomer.

11. A valve assembly as claimed in claim 7, 8 or 9 wherein said yieldable material is initially in a form capable of being injected into said cavity means under a sufficient amount of pressure to seal against a pressure of at least 300 mm Hg from the blood.

12. A valve assembly as claimed in claim 7, 8 or 9 wherein the material of said flattened sleeve means is woven polyester.

13. Apparatus for medical use in a pressurized fluid system associated with a living body comprising
insertable fluid engaging means for exterior insertion into communication with the pressurized fluid and
a valve assembly biased into a closed condition for sealingly containing the pressurized fluid in communication therewith and movable into a seal maintaining open condition in response to the insertion of said insertable fluid engaging means therethrough,
said valve assembly including a body of elastomeric material having flattened sleeve means therein defining a slit presenting opposed surfaces interengaged when said valve assembly is in said closed condition and spaced apart when said valve assembly is in said open condition, said insertable fluid engaging means having a tapered end construction suitable for gradually moving said opposed surfaces from said closed interengaged condition into said open spaced apart condition in response to the insertion of said insertable fluid engaging means therethrough, said insertable fluid engaging means including an exterior periphery configured to be biasingly engaged in sealing relation by said opposed surfaces when the latter are in said open spaced apart condition,
said valve assembly further including means operable in addition to the bias provided by the elastomeric material of said body for yieldably biasing said opposed surfaces into sealed relation when in said closed interengaged condition and into sealed relation to the exterior periphery of said insertable fluid engaging means when in said open spaced apart condition, said additional biasing means including cavity means having a yieldable material under pressure therein so located with respect to said flattened sleeve means as to transmit the pressure thereof as the additional bias of the opposed surfaces into sealed relation when in said closed interengaged condition and into sealed relation with the exterior periphery of said insertable fluid engaging means when in said open spaced apart condition.

14. Apparatus as defined in claim 13 wherein the fluid of said fluid system is blood and wherein said flattened sleeve means is made of woven vascular prosthesis material having a coefficient of friction with respect to the material forming the exterior periphery of said insertable fluid engaging means which is less than that of said elastomeric material.

15. Apparatus as defined in claim 14 wherein said body of elastomeric material is mounted within an extracorporeal end of a percutaneous cannula and said insertable fluid engaging means comprises a trocar cooperable with said cannula.

16. Apparatus as defined in claim 14 wherein said body of elastomeric material constitutes a subcutaneous implant and said insertable fluid engaging means comprises a percutaneous cannula and trocar assembly, said trocar providing said tapered end construction, said cannula providing said exterior periphery, said exterior periphery having a biconvex lens-shaped cross-sectional configuration.

17. Apparatus as defined in claim 16 wherein said exterior periphery includes an initial portion of substantially constant cross-sectional configuration dimensions and a shorter final portion which gradually increases in cross-sectional configuration dimensions in a direction toward the extracorporeal end of said cannula.

18. Apparatus as claimed in claim 13, 14, 15, 16 or 17 wherein said elastomeric body is manufactured from a cured silicone elastomer and the yieldable material within said cavity means is selected from the group consisting of a cured silicone elastomer, a polydiorganosiloxane fluid which is substantially impermeable to the silicone elastomer body and vegetable oils.

19. Apparatus as claimed in claim 13, 14, 15, 16 or 17 wherein said cavity means includes opposed cavities.

20. Apparatus as claimed in claim 13, 14, 15, 16 or 17 wherein said yieldable material is a cured silicone elastomer.

21. Apparatus as claimed in claim 13, 14, 15, 16 or 17 wherein said yieldable material is initially in a form capable of being injected into said cavity means under a sufficient amount of pressure to seal against a pressure of at least 300 mm Hg from the fluid system.

22. Apparatus as claimed in claim 13, 14, 15, 16 or 17 wherein the material of said flattened sleeve means is polyester.

23. The improvement as claimed in claim 1, 2 or 3 wherein said opposed surfaces of said sleeve means are formed by a material having a coefficient of friction with respect to the material of the cannula less than that of said elastomeric material.

24. Apparatus as claimed in claim 7, 8 or 9 wherein said opposed surfaces of said sleeve means are formed by a material having a coefficient of friction with respect to the material of the cannula less than that of said elastomeric material.

* * * * *